United States Patent [19]

Vasiliou et al.

[11] Patent Number: 4,761,285

[45] Date of Patent: Aug. 2, 1988

[54] COMPOSITION FOR RELIEF AND TREATMENT OF HEMORRHOIDS

[75] Inventors: Anna Vasiliou, Larisa, Greece; Athanasios Vasiliou, 450 East 800 S., Salt Lake City, Utah 84111

[73] Assignee: Athanasios Vasiliou, Salt Lake City, Utah

[21] Appl. No.: 923,877

[22] Filed: Oct. 28, 1986

[51] Int. Cl.⁴ ............................................. A61K 35/78
[52] U.S. Cl. ................................. 424/195.1; 514/882
[58] Field of Search ...................... 424/195.1; 512/882

[56] References Cited

U.S. PATENT DOCUMENTS

| | | | |
|---|---|---|---|
| 3,608,074 | 9/1971 | Rocher | 424/195.1 |
| 3,935,310 | 1/1976 | Homan | 424/195.1 |
| 4,192,866 | 3/1980 | Anderson | 424/154 |
| 4,193,986 | 3/1980 | Cox | 424/28 |
| 4,261,986 | 4/1981 | Alvarez | 514/180 |
| 4,383,984 | 5/1983 | Alarie | 424/1 |

*Primary Examiner*—John Rollins
*Attorney, Agent, or Firm*—Jon C. Christiansen

[57] ABSTRACT

A composition comprising Leptandra Culver's root, chick-peas and grape seeds. The composition can be enhanced with honey, cinnamon and/or oil. The composition is useful for the relief and treatment of hemorrhoids and hemorrhoidal symptoms. The composition can also be used as an herbal food supplement for dietary and nutritional purposes.

20 Claims, No Drawings

COMPOSITION FOR RELIEF AND TREATMENT OF HEMORRHOIDS

INTRODUCTION

This invention relates to a composition for the relief and treatment of hemorrhoids and hemorrhoidal symptoms. Hemorrhoids are a common affliction of the anorectal area of the human body. Hemorrhoids are soft, irregular venous abnormalities occurring in the anorectal area. Hemorrhoids often cause bleeding, itching, soreness and other discomfort. This invention is applicable to both external hemorrhoids and internal hemorrhoids.

Compositions for the relief and treatment of hemorrhoids are known. Consider, for example, the following patents (all of which are incorporated into this disclosure by this reference):

U.S. Pat. No. 3,608,074 ("Pharmaceutical Compositions and Method of Making the Same"—Yves Rocher)
U.S. Pat. No. 3,935,310 ("Remedy for Treatment of Hemorrhoids"—John D. Homan)
U.S. Pat. No. 4,192,866 ("Anorectal Medication"—Ralph Anderson)
U.S. Pat. No. 4,261,981 ("Medical Compound Produced from Ragweed"—Sam Humphrey)
U.S. Pat. No. 4,383,986 ("Hemorrhoidal Compositions"—Darius D. Dubash, et al.)

In addition to its usefulness for the relief and treatment of hemorrhoids, the composition of this invention can also be used to relieve constipation or as an herbal food supplement eaten for dietary and nutritional purposes.

It is an objective of this invention to provide an edible composition that can be taken orally for the relief and treatment of internal hemorrhoids and hemorrhoidal symptoms. It is another objective of this invention to provide a composition that can be applied to external hemorrhoidal areas for the relief and treatment of external hemorrhoids and hemorrhoidal symptoms. It is a further objective of this invention to provide a composition that can be used to relieve constipation. It is yet a further objective of this invention to provide an herbal food supplement that can be eaten for dietary and nutrition purposes. These objectives and other objectives, aspects and advantages of this invention will be clear to a person of ordinary skill in the art upon reading this disclosure.

SUMMARY OF THIS INVENTION

The composition of this invention is a combination of Leptandra Culver's root, chick-peas and grape seeds. The composition is useful for the relief and treatment of hemorrhoids and hemorrhoidal symptoms and of constipation. The composition is also useful as an herbal food supplement for dietary and nutritional purposes. The composition can be enhanced by adding honey, cinnamon and/or oil.

DETAILED DESCRIPTION OF THE INVENTION

The composition of this invention is a combination of Leptandra Culver's root, chick-peas and grape seeds. This basic combination can be enhanced by the addition of honey, oil and/or cinnamon. The composition can be taken orally for the relief and treatment of internal hemorrhoids and constipation. The composition can also be eaten as an herbal food supplement. In other embodiments of the invention, the composition can be applied as a salve to an external hemorrhoidal area.

Leptandra Culver's root is an herb known to herbal experts. See, for example, M. Brieve, "A Modern Herbal, the Medicinal, Culinary, Cosmetic and Economic Properties, Cultivation and Folk-Lore of Herbs, Grasses, Fungi, Shrubs and Trees with all their Modern Scientific Uses", Vol. 1, page 111 (Dover Publications, Inc., New York). (The foregoing is incorporated into this disclosure by this reference). Leptandra Culver's root is also known under the following names: black root, Culveris root, Culver's physic, physic root, Leptandra-Wurzel, Skarfi and Ellevoros Melas. Skarfi and Ellevoros Melas are Greek names for Leptandra Culver's root. The plant itself is a tall, herbaceous perennial. The useful portions of the plant are the rhizome and roots and all reference to Leptandra Culver's root in this disclosure and the appended claims shall mean the rhizome and/or root portions. Preferably, the Leptandra Culver's root is dried (rather than using fresh rhizome or root in the practice of this invention).

The chick-pea plant is an annual plant of the pea family grown in many parts of the world for its nutritious seeds or peas. These seeds or peas are referred to in this disclosure and the appended claims as chick-peas. Preferably, the chick-peas used in the composition of this invention are dried rather than fresh.

With the obvious exception of seedless grapes, any member of the grape genus, Vitis (family Vitaceae), can be used to provide the grape seeds used in the composition of this invention. Among the very many varieties and species of grapes any of the seeded kinds commonly used as table fruits or for the production of raisins or to make juice or wine can provide grape seeds useful in the practice of this invention. Although the invention is not limited thereto, the inventors prefer the use of seeds from a common table fruit grape or a commercial wine grape. Preferably, the grapes used in the composition of this invention are dried rather than fresh.

The inventive composition can be enhanced with the addition of honey as an additional component of the composition. Honey adds substance and flavor to the composition. The honey of any bee or floral type can be used. Preferably, a commercially available liquid honey is used.

The inventive composition can also be enhanced with the addition of cinnamon as an additional component of the composition. Cinnamon is a well known light brown spice having a delicately fragrant aroma and a warm, sweet flavor. Cinnamon adds flavor to the composition and is a desirable additional component when the composition is taken orally.

If the inventive composition is to be applied as a salve to a hemorrhoidal area, oil can be added as an additional component of the composition to facilitate formation of the salve and its external application to the hemorrhoidal area. The preferred oil is olive oil (a high grade or quality of olive oil is recommended). Other oils, such a palm oil, vegetable oils, cooking oils, etc. can be used. Substances other than oil can also be used in the composition as a vehicle to facilitate formation of a salve and its external application to the hemorrhoidal area.

The inventive composition is any combination of Leptandra Culver's root, chick-peas and grape seeds. Although the invention is not limited thereto, general and preferred content ranges are given below in terms of parts by weight (wt.) per 100 parts by weight (wt.) of Leptandra Culver's root.

| Component | General Range (parts by wt.) | Preferred Range (parts by wt.) (edible) | Preferred Range (parts by wt.) (salve) |
|---|---|---|---|
| Leptandra Culver's root | 100 | 100 | 100 |
| Chick-peas | 5–100 | 20–50 | 12–44 |
| Grape seeds | 2–50 | 8–16 | 10–26 |

If cinnamon is used, it is added to taste or, if as a coating, in such amount as is sufficient to coat the composition in whatever shape it may be in. If honey is used as a component of the edible composition, its content will generally range from about 50 to about 500 parts by weight and will preferably range from about 150 to about 220 parts by weight (per 100 parts by weight of Leptandra Culver's root). If honey is used in a composition salve for external hemorrhoids, it is generally used in an amount chosen by the particular practitioner as his/her preference to facilitate formation and application of the salve. If oil is used in a composition salve for external hemorrhoids, it also is generally used in such amount as is preferred by the particular practitioner to facilitate formation and application of the salve.

With the assistance, direction and benefit of this disclosure, a person of ordinary skill in the art may seek to extract or isolate from the above-identified components (or may seek to derive, make or synethesize) the physiologically active substances, chemicals or subcomponents found in the inventive composition which are physiologically effective for relief or treatment of hemorrhoids or hemorrhoidal symptoms. Such physiologically active and effective substances, chemicals and subcomponents are deemed the equivalents of the above-identified components and the inventive composition and are intended to fall within the scope of the appended claims.

DETAILED EXAMPLES

This first example describes the procedure for producing the inventive composition, with honey and cinnamon, in an edible pill-shaped form. Dried Leptandra Culver's root, dried chick-peas and dried grape seeds are separately ground or chopped into small pieces (preferably a powder). A conventional household blender or commercial grinding or blending apparatus can be used. The Leptandra Culver's root, chick-peas and grape seeds are then combined and mixed or blended together to form a mixture in the amount shown below:

| Leptandra Culver's root - | 16 grams |
|---|---|
| Chick-peas - | 5 grams |
| Grape seeds - | 2 grams |

About 30 grams of liquid honey is added to, and mixed or blended with, the mixture. Spherical shaped pills about ½ cm in diameter are formed by hand or machine from the mixture. Other shapes can also be formed if desired. Cinnamon is sprinkled on a flat area and the pills are rolled over the cinnamon to coat the pills with cinnamon. The coated pills are allowed to dry for about 48 hours in open air at room temperature.

When used for relief and treatment of hemorrhoids and hemorrhoidal symptoms (or for constipation), the average person will take about two pills per day (i.e. one every 12 hours). Depending on the particular person and the severity of the hemorrhoidal condition, the foregoing dosage may vary. When used only as an herbal food supplement for dietary or nutritional purposes, the average person will take the pills at a rate of about one per day to one per week.

This second example describes the procedure for producing the inventive composition, with honey and olive oil, in the form of a salve for application to external hemorrhoidal areas. The Leptandra Culver's root, chick-peas and grape seeds are ground (or chopped), combined and mixed (or blended) as provided in the first example but in the following amounts:

| Leptandra Culver's root - | 26 grams |
|---|---|
| Chick-peas - | 6 grams |
| Grape seeds - | 4 grams |

One tablespoon of liquid honey and two tablespoons of high grade olive oil are added to, and mixed or blended with, the mixture of Leptandra Culver's root, chick-peas and grape seeds to form a salve. The salve is applied to the external hemorrhoidal area for relief and treatment. It is recommended that the area be covered with a bandage after application of the salve for about 15 to 20 minutes. Typically, the salve is applied twice a day (e.g. morning and evening). Depending on the particular person and the severity of the hemorrhoidal condition, the salve can be applied more or less frequently.

It should be noted that substances other than honey and oil can be used as a "vehicle" for facilitating salve formation and application to the external hemorrhoidal area. Thus such substances can be used in the practice of this invention. Although such substances are not preferred and lack the advantages of honey and oil, compositions with such other substances in combination with Leptandra Culver's root, chick-peas and grape seeds are within the scope of the appended claims.

The foregoing examples of this invention and this disclosure as a whole so fully reveal the general nature of this invention that others can, by applying current knowledge, readily modify such examples or description and/or adapt them for various applications without departing from the generic concept of this invention, and therefore, such adaptations and modifications should and are intended to be comprehended within the meaning and range of equivalents of the appended claims, which claims define subject matter regarded to be our invention.

NOTICE

The disclosure set forth herein (1) is given strictly for patent purposes, (2) may not be relied upon for any other purpose, and (3) is not intended as a substitute for medical advise or information from your duly licensed medical doctor.

We claim:

1. A composition comprising the following components: Leptandra Culver's root, chick-peas and grape seeds.

2. A composition for the relief and treatment of internal hemorrhoids and hemorrhoidal symptoms in accordance with claim 1 wherein said composition is edible and is eaten to effect said relief and treatment.

3. An edible composition for the relief and treatment of internal hemorrhoids and hemorrhoidal symptoms in accordance with claim 2 further comprising at least one component selected from the group consisting of honey and cinnamon.

4. An edible composition for the relief and treatment of internal hemorrhoids and hemorrhoidal symptoms in accordance with claim 2 wherein said chick-peas content ranges from about 5 to about 100 parts by weight per 100 parts by weight of Leptandra Culver's root and said grape seeds content ranges from about 2 to about 50 parts by weight per 100 parts by weight of Leptandra Culver's root.

5. An edible composition for the relief and treatment of internal hemorrhoids and hemorrhoidal symptoms in accordance with claim 2 wherein said chick-peas content ranges from about 20 to about 50 parts by weight per 100 parts by weight of Leptandra Culver's root and said grape seeds content ranges from about 8 to about 16 parts by weight per 100 parts by weight of Leptandra Culver's root.

6. An edible composition for the relief and treatment of internal hemorrhoids and hemorrhoidal symptoms in accordance with claim 5 further comprising honey and cinnamon; wherein said Leptandra Culver's root, chick-peas and grapes seeds are dried and have been ground or chopped into small pieces or a powder; wherein said honey is mixed or blended with said Leptandra Culver's root, chick-peas and grape seeds to form a mixture; wherein said mixture is shaped into pills; and wherein said pills are coated with said cinnamon.

7. A composition for the relief and treatment of external hemorrhoids and hemorrhoidal symptoms in accordance with claim 1 wherein said relief and treatment are effected by applying said composition to an external hemorrhoidal area.

8. A composition for the relief and treatment of external hemorrhoids and hemorrhoidal symptoms in accordance with claim 7 in the form of a salve for application to an external hemorrhoidal area and further comprising a vehicle to facilitate the formation of said salve from said components and to facilitate the application of said components to the external hemorrhoidal area.

9. A composition for the relief and treatment of external hemorrhoids and hemorrhoidal symptoms in accordance with claim 8 wherein said vehicle comprises honey.

10. A composition for the relief and treatment of external hemorrhoids and hemorrhoidal symptoms in accordance with claim 8 wherein said vehicle comprises oil.

11. A composition for the relief and treatment of external hemorrhoids and hemorrhoidal symptoms in accordance with claim 8 wherein said chick-peas content ranges from about 5 to about 100 parts by weight per 100 parts by weight of Leptandra Culver's root and said grape seeds content ranges from about 2 to about 50 parts by weight per 100 parts by weight of Leptandra Culver's root.

12. A composition for the relief and treatment of external hemorrhoids and hemorrhoidal symptoms in accordance with claim 8 wherein said chick-peas content ranges from about 12 to about 44 parts by weight per 100 parts by weight of Leptandra Culver's root and said grape seeds content ranges from about 10 to about 26 parts by weight per 100 parts by weight of Leptandra Culver's root.

13. A composition for the relief and treatment of external hemorrhoids and hemorrhoidal symptoms in accordance with claim 12 wherein said vehicle comprises honey and olive oil.

14. A composition in accordance with claim 1 wherein said composition is an edible herbal food supplement.

15. An edible herbal food supplement in accordance with claim 14 further comprising at least one component selected from the group consisting of honey and cinnamon.

16. A method for the relief and treatment of external hemorrhoids and hemorrhoidal symptoms comprising applying the composition of claim 7 to an external hemorrhoidal area of the human body.

17. A method for the relief and treatment of external hemorrhoids and hemorrhoidal symptoms comprising applying the composition of claim 12 to an external hemorrhoidal area of the human body.

18. A method for the relief and treatment of external hemorrhoids and hemorrhoidal symptoms comprising applying the composition of claim 13 to an external hemorrhoidal area of the human body.

19. A method for the relief and treatment of internal hemorrhoids and hemorrhoidal symptoms of the human body comprising eating the composition of claim 2 to effect said relief and treatment.

20. A method for the relief and treatment of internal hemorrhoids and hemorrhoidal symptoms of the human body comprising eating the composition of claim 6 to effect said relief and treatment.

* * * * *